(12) United States Patent
Gerberding et al.

(10) Patent No.: US 6,964,676 B1
(45) Date of Patent: Nov. 15, 2005

(54) STENT SECUREMENT SYSTEM

(75) Inventors: Brent C. Gerberding, Minneapolis, MN (US); David J. Holtan, Rogers, MN (US); Scott M. Hanson, Savage, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/549,286

(22) Filed: Apr. 14, 2000

(51) Int. Cl.⁷ .................................................. A61F 2/06
(52) U.S. Cl. ...................................... 623/1.11; 606/108
(58) Field of Search ............................... 623/1.11, 1.12, 623/1.13, 1.14, 1.15, 1.16, 1.17, 1.18, 1.19, 623/1.2, 1.21, 1.22; 604/96–103; 606/108, 606/191, 192, 194, 195, 198

(56) References Cited

U.S. PATENT DOCUMENTS

| | | | |
|---|---|---|---|
| 4,950,227 A | 8/1990 | Savin et al. ................... 604/8 |
| 5,108,416 A | 4/1992 | Ryan et al. ................. 606/194 |
| 5,403,341 A * | 4/1995 | Solar ........................... 606/198 |
| 5,571,135 A | 11/1996 | Fraser et al. ............... 606/198 |
| 5,593,412 A | 1/1997 | Martinez et al. ........... 606/108 |
| 5,690,642 A | 11/1997 | Osborne et al. ............ 606/108 |
| 5,707,385 A | 1/1998 | Williams ..................... 606/192 |
| 5,944,726 A | 8/1999 | Blaeser et al. .............. 606/108 |
| 5,954,729 A | 9/1999 | Bachmann et al. ......... 606/108 |
| 5,968,069 A * | 10/1999 | Dusbabek et al. ........ 604/96.01 |
| 5,980,530 A | 11/1999 | Willard et al. .............. 606/108 |
| 6,068,634 A | 5/2000 | Cornelius et al. ........... 606/108 |
| 6,123,723 A | 9/2000 | Konya et al. ............... 623/1.11 |
| 6,168,617 B1 * | 1/2001 | Blaeser et al. ............. 623/1.11 |
| 6,221,097 B1 * | 4/2001 | Wang et al. ................ 606/108 |
| 6,287,291 B1 | 9/2001 | Bigus et al. ................ 604/523 |
| 6,330,884 B1 | 12/2001 | Kim ............................ 128/898 |
| 2001/0032009 A1 | 10/2001 | Layne et al. ............... 623/1.13 |

FOREIGN PATENT DOCUMENTS

| | | |
|---|---|---|
| WO | 96/31249 | 10/1996 |
| WO | 00/76425 | 12/2000 |

* cited by examiner

*Primary Examiner*—Vy Bui
(74) *Attorney, Agent, or Firm*—Vidas, Arrett & Steinkraus PA

(57) ABSTRACT

A stent delivery system having a delivery catheter, a stent mounted thereupon and at least one stent retaining sleeve to retain the stent on the catheter prior to stent delivery. At least a portion of the at least one stent retaining sleeve being further characterized as having a plurality of through-holes. The through-holes providing the at least one stent retaining sleeve with reduced radial and columnar strength when compared to a sleeve without through-holes.

23 Claims, 2 Drawing Sheets

STENT SECUREMENT SYSTEM

CROSS-REFERENCE TO RELATED APPLICATIONS

Not Applicable

STATEMENT REGARDING FEDERALLY SPONSORED RESEARCH

Not Applicable

BACKGROUND OF THE INVENTION

The present invention relates to a delivery system in which a catheter carries a stent on its distal end portion. The stent is held in place around the catheter prior to and during percutaneous delivery by means of one and preferably two sleeves. The stent may be self-expanding, such as a NITINOL shape memory stent, or it may be expandable by means of an inflatable portion of the catheter, such as a balloon. The sleeve or sleeves have a plurality of holes which may be bored partially or completely through the material of the sleeve or sleeves. The holes may be mechanically bored or laser bored. The holes are distributed about the surface of the sleeve or sleeves in a uniform pattern but may have a variety of shapes and sizes. The sleeve or sleeves may be composed of an elastic polymer, a non-elastic polymer or a combination thereof.

Stents and stent delivery assemblies are utilized in a number of medical procedures and situations, and as such their structure and function are well known. A stent is a generally cylindrical prosthesis introduced via a catheter into a lumen of a body vessel in a configuration having a generally reduced diameter and then expanded to the diameter of the vessel. In its expanded configuration, the stent supports and reinforces the vessel walls while maintaining the vessel in an open, unobstructed condition.

Both self-expanding and inflation expandable stents are well known and widely available in a variety of designs and configurations. Self-expanding stents must be maintained under a contained sheath or sleeve(s) in order to maintain their reduced diameter configuration during delivery of the stent to its deployment site. Inflation expandable stents are crimped to their reduced diameter about the delivery catheter, then maneuvered to the deployment site and expanded to the vessel diameter by fluid inflation of a balloon positioned between the stent and the delivery catheter. The present invention is particularly concerned with delivery and deployment of inflation expandable stents, although it is generally applicable to self-expanding stents when used with balloon catheters.

In advancing an inflation expandable stent through a body vessel to the deployment site, there are a number of important considerations. The stent must be able to securely maintain its axial position on the delivery catheter without translocating proximally or distally and especially without becoming separated from the catheter. The stent, particularly its distal and proximal ends, must be protected to prevent distortion of the stent and to prevent abrasion and/or reduce trauma of the vessel walls.

Inflation expandable stent delivery and deployment assemblies are known which utilize restraining means that overlie the stent during delivery. U.S. Pat. No. 4,950,227 to Savin et al., relates to an inflation expandable stent delivery system in which a sleeve overlaps the distal or proximal margin (or both) of the stent during delivery. During inflation of the stent at the deployment site, the stent margins are freed of the protective sleeve(s). U.S. Pat. No. 5,403,341 to Solar, relates to a stent delivery and deployment assembly which uses retaining sheaths positioned about opposite ends of the compressed stent. The retaining sheaths of Solar are adapted to tear under pressure as the stent is radially expanded, thus releasing the stent from engagement with the sheaths. U.S. Pat. No. 5,108,416 to Ryan et al., describes a stent introducer system which uses one or two flexible end caps and an annular socket surrounding the balloon to position the stent during introduction to the deployment site. The entire contents of each of the patents cited herein is hereby incorporated by reference.

This invention provides an improvement over the prior art, by providing a stent delivery system wherein the stent retaining sleeves have a reduced radial and columnar strength thereby allowing a delivery catheter to deploy a balloon expandable stent at lower pressures with greater consistency than otherwise would be possible. The lower strength of the sleeves also allows the sleeves to be readily retracted from the stent without additional lubrication, however lubricants may still be applied to a stent delivery catheter using the sleeves described.

BRIEF SUMMARY OF THE INVENTION

This invention provides for a stent delivery system wherein the stent is held onto the stent delivery catheter with one or more tubular shaped stent retaining sleeves. The stent retaining sleeves contain a plurality of through-holes which may be distributed in a predetermined pattern on at least a portion of the sleeve tube. Alternatively, the through-holes may be distributed irregularly on the at least a portion of the sleeve tube.

The through-holes may have a variety of size and shape, or may be uniformly sized and shaped. The through-holes may also be characterized as dimples, indentations, slits or cuts made through the sleeve tube surface.

The presence of the through-holes provide the sleeve or sleeves with reduced radial and columnar strength allowing the sleeve(s) to be more easily retracted and have the capacity to release a stent with greater consistency under reduced pressure, when compared to prior stent retaining sleeves.

BRIEF DESCRIPTION OF THE SEVERAL VIEWS OF THE DRAWINGS

A detailed description of the invention is hereafter described with specific reference being made to the drawings in which.

DETAILED DESCRIPTION OF THE INVENTION

Figure 1:
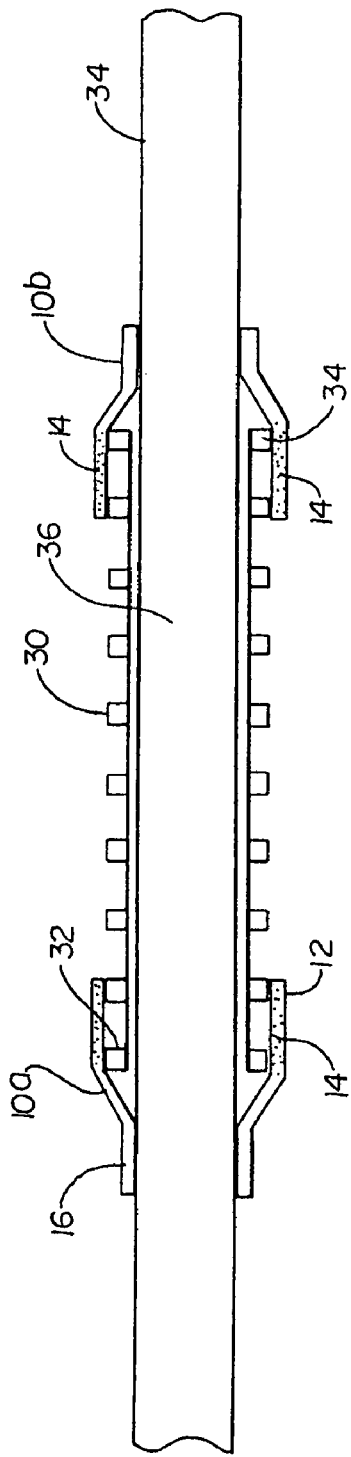
FIG. 1 is a perspective view of a stent delivery catheter equipped with a pair of stent retaining sleeves having a plurality of bored through holes in the uninflated position.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

Figure 2:
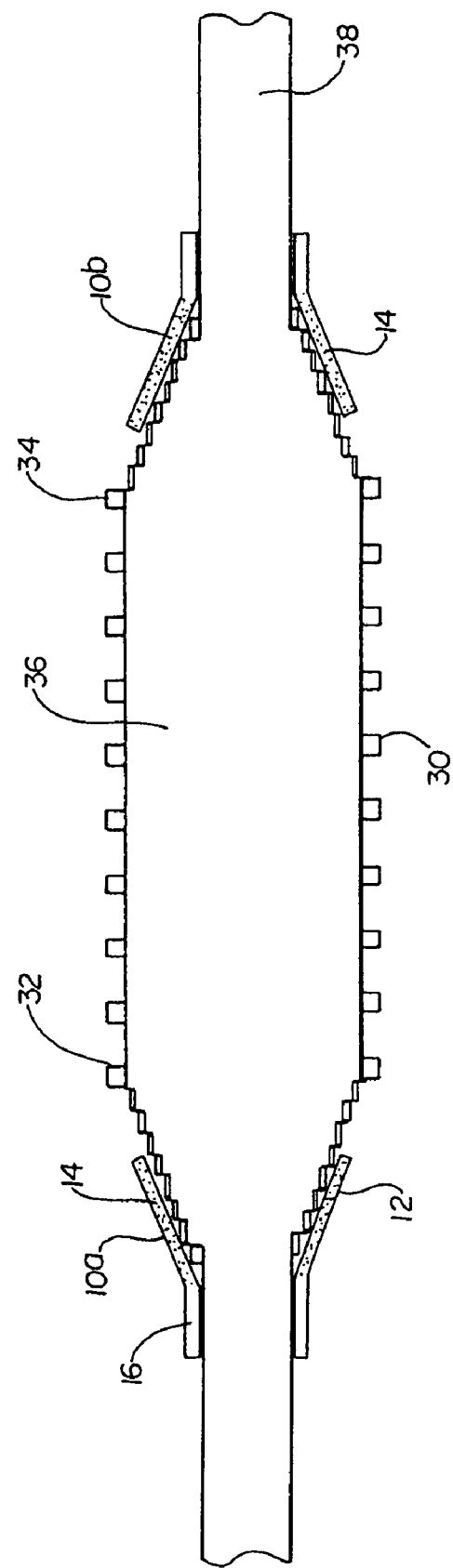
FIG. 2 is a perspective view of the stent delivery catheter shown in FIG. 1 in the inflated position.

FIGS. 1 and 2 show a first embodiment of a stent delivery system wherein a stent 30 is mounted upon a stent delivery catheter 38. FIG. 1 shows the stent delivery system prior to stent delivery. FIG. 2 shows the stent delivery system during stent delivery. As may be seen in both figures, a pair of sleeves 10a and 10b are employed to retain the stent ends 32 and 34 on an inflatable portion 36 of a delivery catheter 38 prior to stent delivery.

As best seen in FIG. 2 when the inflatable portion 36 is inflated the stent 30 is expanded radially. As the stent 30 expands the stent ends 32 and 34 are pulled away from sleeves 10a and 10b. When the inflatable portion 36 is inflated to a predetermined extent, the stent ends 32 and 34 will be completely freed from the sleeves 10a and 10b.

The sleeves 10a and 10b of the present invention will typically be distinguished by having a stent retaining portion 12 which contains a plurality of through-holes 14, and an anchored portion 16 which lacks through-holes.

The through-holes 14 which are present in the sleeves 10a and 10b provide the respective sleeve with reduced radial and columnar strength relative to a sleeve that does not have the through-holes. The reduced radial strength of sleeves 10a and 10b allows the sleeves to be withdrawn from stent 30 with less radial expansion than previous sleeve types. Consequently, a balloon expandable stent may be released from the stent retaining sleeves 10a and 10b with less inflation pressure than previously required. For example, a particular example of the present invention which includes a pair of sleeves having through-holes, may be withdrawn from the surface of a stent when the stent is expanded under approximately 3.5 atmospheres of pressure. On the other hand, some sleeves without through-holes may require between 4.5 to 5 atmospheres of pressure to be withdrawn from the stent surface.

In addition, the reduced columnar strength of the sleeves 10a and 10b causes the sleeves to have a reduced capacity to be retained upon stent ends 32 and 34 as they expand outward. As a result, in the present stent delivery system there may be no need to provide lubrication between sleeves 10a, 10b and stent ends 32, 34 to release the stent during expansion. Although a slip coat may still be used for improved performance.

Figure 3:
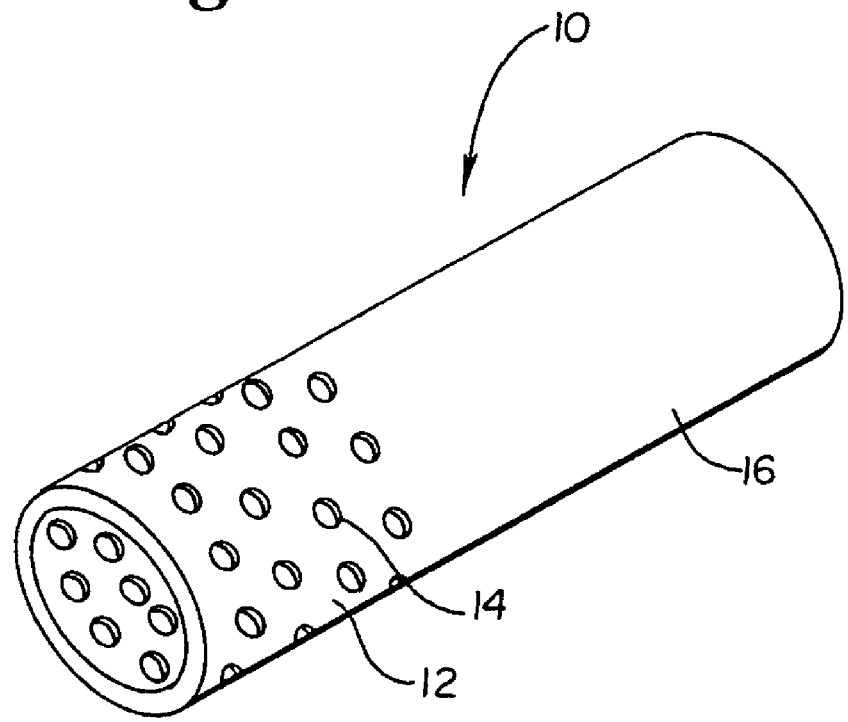
FIG. 3 is a perspective view of an embodiment of a tubular sleeve having a portion with a plurality of bored through-holes.

As may be seen in FIG. 3, the through-holes 14 may be uniformly distributed about stent retaining portion 12. Alternatively, the through-holes 14 may be distributed randomly and/or they may be distributed about the entire sleeve 10. The through-holes 14 may have a variety of sizes and shapes, some examples of suitable hole shapes include ellipsoids such as circles and ovals, but non-uniform shapes may be used as well. Preferably, the through-holes 14 have a uniform circular shape and diameter such as those shown in FIG. 3. Typically, the through-holes 14 will have a diameter within the range of 10–1000 microns and preferably within the range of 75–100 microns, however other sizes may also be utilized.

The through-holes 14 may be bored into or through the sleeve 10 using a variety of boring methods. Preferably, in order to achieve uniform hole diameter and shape through-holes 14 are laser bored. Mechanical boring, such as by a mechanical drill and suitably sized bit may also be utilized.

Figure 4:
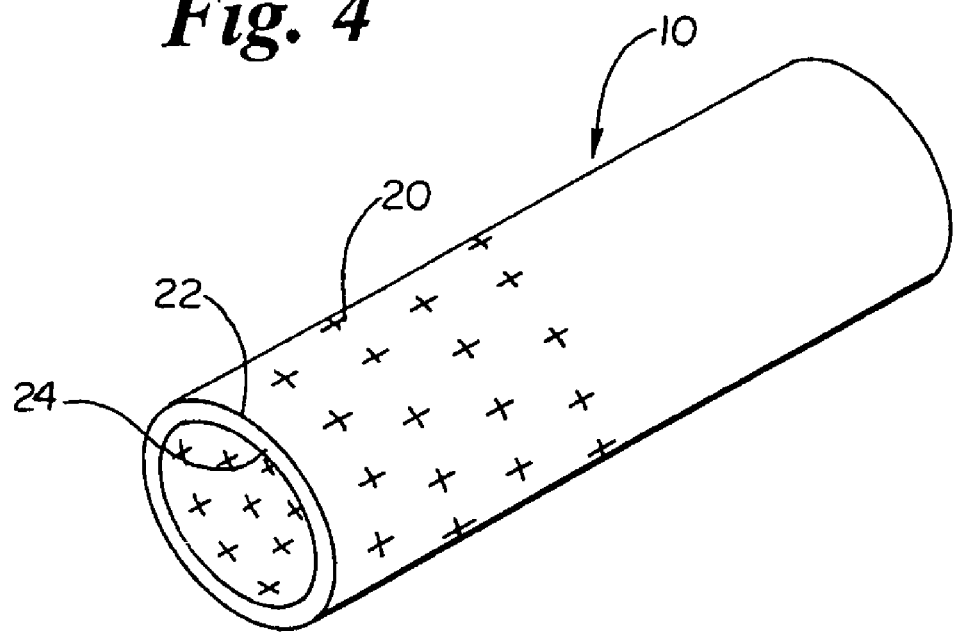
FIG. 4 is a perspective view of a second embodiment of a tubular sleeve having a portion with a plurality of through-holes, the through-holes being cuts.

In the embodiment shown in FIG. 4, the through-holes are best characterized as micro-cuts 20. The micro-cuts 20 are made by making an incision on the outside surface 22 of the sleeve 10 which passes through the outside surface 22 to the inside surface 24. When the sleeve 10 is placed on a catheter such as shown in FIG. 1, the user may find it desirable or necessary to apply a lubricant to the stent 30 which underlies the sleeves 10a and 10b. The micro-cuts 20 provide the sleeves 10a and 10b with the ability to wick a lubricant or other fluid through the outside surface 22 to the inside surface 24 where it will lubricate the stent.

In all embodiments the sleeve 10 may be constructed from a variety of components. Preferably, sleeve 10 is made of an elastic polymer or polymers. The sleeve 10 may also contain non-elastic polymers exclusively or in part, but it may be necessary to process the non-elastic polymers to obtain the more desirable elastic characteristics. In a more preferred embodiment the sleeve 10 is constructed at least in part of TECOTHANE material and/or CARBOTHANE material. TECOTHANE AND CARBOTHANE are well known trademarked names for respective classes of biocompatable medical grade polyurethanes, both of which are available from Thermedics Inc., located in Woburn, Mass. TECOTHANE is an aromatic polyether based polyurethane having a durometer hardness range, as measured by the Shore D scale, of 75A to 77D. CARBOTHANE is an aliphatic polycarbonate based polyurethane having a durometer hardness range 73A and 75D.

In addition to being directed to the embodiments described above and claimed below, the present invention is further directed to embodiments having different combinations of the features described above and claimed below. As such, the invention is also directed to other embodiments having any other possible combination of the dependent features claimed below.

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A stent delivery system comprising:
   a stent delivery catheter, the stent delivery catheter having a stent mounting region;
   a stent disposed about the stent mounting region, the stent having an unexpanded position and an expanded position and a first end and a second end; and
   a stent retaining sleeve anchored to the stent delivery catheter and disposed about at least a portion of the stent in the unexpanded position, at least a portion of the stent retaining sleeve being further characterized as having a plurality of through-holes, the plurality of through-holes being spaced in the stent retaining sleeve such that the stent retaining sleeve resists tearing when the stent is expanded to its expanded position and that the plurality of through-holes remain formed in the stent retaining sleeve and the stent retaining sleeve remains untorn after the stent has been expanded to its expanded position, the stent retaining sleeve further comprising a first stent retaining sleeve and a second stent retaining sleeve, the first and second stent retaining sleeves each having a stent retaining portion and an anchored portion, the stent retaining portion of the first stent retaining sleeve at least partially disposed about the first end of the stent in the unexpanded position, the anchored portion of the first stent retaining sleeve retained about the stent delivery catheter, the stent retaining portion of the second stent retaining sleeve at least partially disposed about the second end of the stent in the unexpanded position, the anchored portion of the second stent retaining sleeve retained about the stent delivery catheter.

2. The stent delivery system of claim 1 wherein the at least a portion of the stent retaining sleeves comprises the stent retaining portion of the respective sleeve.

3. The stent delivery system of claim 1 wherein the plurality of through-holes are distributed about the stent retaining sleeves in a predetermined pattern.

4. The stent delivery system of claim 1 wherein the plurality of through-holes are distributed about the stent retaining portion of the first and second sleeves respectively in a predetermined pattern.

5. The stunt delivery system of claim 4 wherein the plurality of through-holes are uniformly sized and shaped.

6. The stent delivery system of claim 1 wherein the plurality of through-holes have uniform diameters.

7. The stent delivery system of claim 1, the plurality of through-holes each having individual diameters between 75–100 microns.

8. The stent delivery system of claim 1 wherein the plurality of through-holes are formed with a laser.

9. The stent delivery system of claim 1 wherein the plurality of through-holes are mechanically bored.

10. The stent delivery system of claim 1 further comprising a lubricant, the lubricant applied to at least a portion of the stent delivery catheter through the plurality of through-holes.

11. The stent delivery system of claim 1 wherein the stent retaining sleeve is constructed from one or more elastic polymers.

12. The stent delivery system of claim 1 wherein the stent retaining sleeve is constructed from one or more non-elastic polymers.

13. The stent delivery system of claim 1 wherein the stent retaining sleeve is constructed from a combination of one or more elastic polymers and one or more non-elastic polymers.

14. The stent delivery system of claim 1 wherein the at least one stent retaining sleeve is constructed from materials selected from the group consisting of aromatic polyether based polyurethane, aliphatic polycarbonate based polyurethane and any combinations thereof.

15. The stent delivery system of claim 1 wherein the stent delivery catheter has an inner diameter between 0.028 inches and 0.045 inches.

16. The stent delivery system of claim 1 wherein the stent retaining sleeve is at least 10 mm long.

17. A stent delivery system with reduced deployment pressures comprising:
a stent delivery catheter, the stent delivery catheter having a stent mounting region;
a stent disposed about the stent mounting region, the stent having a unexpanded position and an expanded position, the stent having a first end and a second end;
a pair of stent retaining sleeves having reduced radial and columnar strength, a stent retaining portion of each stent retaining sleeve disposed about a stent end when the stent is in the unexpanded position, an anchored portion of each stent retaining sleeve secured to the stent delivery catheter, at least a portion of each of the stent retaining sleeves having a plurality of radial and columnar strength reducing through-holes, when the stent is in the expanded position each of the stent retaining sleeves releasing the stent from the stent mounting region, the plurality of radial and columnar strength reducing through-holes being spaced in the stent retaining sleeves such that the stent retaining sleeves resist tearing when the stent is expanded to its expanded position and that the plurality of radial and columnar strength reducing through-holes remain formed in the stent retaining sleeve and the stent retaining sleeves remain untorn after the stent has been expanded to its expanded position.

18. The stent delivery system of claim 17 wherein the pair of stent retaining sleeves having an inner diameter no greater than 0.08 inches.

19. A stent delivery system comprising:
a) a stent delivery catheter, the stent delivery catheter having a stent mounting region;
b) a stent disposed about the stent mounting region, the stent having an unexpanded position and an expanded position, a first end, a second end and a center portion positioned between the first end and the second end of the stent;
c) a first stent retaining sleeve disposed about at least a portion of the stent delivery catheter, the first stent retaining sleeve having a first end and a second end, wherein the second end of the first stent retaining sleeve extends over the first end of the stent in its unexpanded state position, but does not extend over the center portion of the stent leaving the center portion of the stent uncovered by the first stent retaining sleeve during delivery of the stent, at least a portion of the first stent retaining sleeve being further characterized as having a plurality of through-holes, the plurality of through-holes being spaced in the first stent retaining sleeve such that the first stent retaining sleeve resists tearing when the stent is expanded to its expanded position and that the plurality of through-holes remain formed in the first stent retaining sleeve and the first retaining sleeve remains untorn after the stent has been expanded to its expanded position.

20. The stent delivery system of claim 19, further comprising a second stent retaining sleeve disposed about at least a portion of the stent delivery catheter, the second stent retaining sleeve having a first end and a second end, wherein the second end of the second stent retaining sleeve extends over the second end of the stent in its unexpanded state position, but does not extend over the center portion of the stent leaving the center portion of the stent uncovered by the second stent retaining sleeve during delivery of the stent.

21. The stent delivery system of claim 20, at least a portion of the second stent retaining sleeve being further characterized as having a plurality of through-holes.

22. The stent delivery system of claim 19, wherein the first end of the first stent retaining sleeve is anchored to the stent delivery catheter.

23. The stent delivery system of claim 21, wherein the first end of the second stent retaining sleeve is anchored to the stent delivery catheter.

* * * * *